(12) United States Patent
Gradl et al.

(10) Patent No.: US 7,501,233 B2
(45) Date of Patent: Mar. 10, 2009

(54) METHOD FOR MEASURING THE VITALITY OF CELLS

(75) Inventors: Gabriele Gradl, Berlin (DE); Thomas Schnelle, Berlin (DE); Torsten Müller, Berlin (DE); Christoph Reichle, Berlin (DE)

(73) Assignee: Perkinelmer Cellular Technologies Germany GmbH, Hamburg (DE)

( * ) Notice: Subject to any disclaimer, the term of this patent is extended or adjusted under 35 U.S.C. 154(b) by 418 days.

(21) Appl. No.: 10/416,278

(22) PCT Filed: Nov. 9, 2001

(86) PCT No.: PCT/EP01/12997

§ 371 (c)(1),
(2), (4) Date: Sep. 3, 2003

(87) PCT Pub. No.: WO02/38567

PCT Pub. Date: May 16, 2002

(65) Prior Publication Data

US 2004/0053211 A1      Mar. 18, 2004

(30) Foreign Application Priority Data

Nov. 10, 2000   (EP)   ................... 00124662

(51) Int. Cl.
*C12Q 1/00*     (2006.01)
(52) U.S. Cl. .......................................... 435/4
(58) Field of Classification Search ............... None
See application file for complete search history.

(56) References Cited

U.S. PATENT DOCUMENTS

| | | | |
|---|---|---|---|
| 5,985,883 A | 11/1999 | Pees | |
| 6,004,767 A | 12/1999 | Crouch et al. | |
| 6,117,876 A | 9/2000 | Pees et al. | |

FOREIGN PATENT DOCUMENTS

| | | |
|---|---|---|
| EP | 0 945 453 A1 | 9/1999 |
| FR | 2 784 381 A1 | 9/1999 |
| WO | WO 98/02579 A1 | 1/1998 |
| WO | WO 98/46607 A1 | 10/1998 |
| WO | WO 98/55615 A1 | 12/1998 |
| WO | WO 99/09208 A1 | 2/1999 |
| WO | WO 99/18856 A1 | 4/1999 |

OTHER PUBLICATIONS

Gimsa et al. A Unified Resistor-Capacitor Model for Impedance, Dielectrophoresis, Electrorotation, and Induced Transmembrane Potential; Biophysical Journal, vol. 75 (1998) pp. 1107-1116.*
Dopp et al. Dielectric Changes in Membrane Properties and Cell Interiors of Human Mesothelial Cells in Vitro After Crocidolite Asbestos Exposure; Environmental Health Perspectives, vol. 108, No. 2 (2000) pp. 153-158.*
Hodgson et al. Determination of the Viability of *Escherichia coli* at the Single Organism Level by Electrorotation; Clinical Chemistry, vol. 44, No. 9 (1998) pp. 2049-2051.*
Kaler et al. Spinning Response of Yeast Cells to Rotating Electric Fields; Journal of Biological Physics, vol. 13 (1985) pp. 69-73.*
Bonincontro et al., "Apoptosis Dependent Decrease of the Intramembrane Ion Traffic in Cultured Mouse Fibroblasts Shown by Conductivity Dispersion," *Bioscience Reports*, vol. 17, No. 6 (1997).
De Gasperis et al., "Automated electrorotation: dielectric characterization of living cells by real-time motion estimation," *Meas. Sci. Technol.*, 9, 518-529 (1998).
Douglas et al., "A simplified method for the coordinate examination of apoptosis and surface phenotype of murine lymphocytes," *Journal of Immunological Methods*, 188, 219-228 (1995).
Elstein et al., "Comparison of Cellular and Nuclear Flow Cytometric Techniques for Discriminating Apoptotic Subpopulations," *Experimental Cell Research*, 211, 322-331 (1994).
Gradl et al., "Micro-Electrode Systems for Cell Analysis," *European Journal of Cell Biology*, Suppl. 49, vol. 78, 80 (1999).
Hölzel, "Nystatin-induced changes in yeast monitored by time-resolved automated single cell electrorotation," *Biochimica et Biophysica Acta*, 1425, No. 2, 311-318 (Oct. 1998).
Irimajiri et al., "Dielectric Modeling of Biological Cells. Models and Algorithm," *Bull. Inst. Chem. Res.*, vol. 69, No. 4 (1991).
Koopman et al., "Annexin V for Flow Cytometric Detection of Phosphatidylserine Expression on B Cells Undergoing Apoptosis," *Blood*, vol. 84, No. 5, pp. 1415-1420 (Sep. 1, 1994).
Leist et al., "Murine Hepatocyte Apoptosis Induced In Vitro and In Vivo by TNF—$\alpha$ Requires Transcriptional Arrest," *The Journal of Immunology*, 153, p. 1778-1788 (1994).
Orrenius, "Apoptosis: molecular mechanisms and implications for human disease," *J. Internal Medicine*, 237, p. 529-533 (1995).
Pethig et al., "Applications of dielectrophoresis in biotechnology," *Trends in Biotechnology*, 15, p. 426-432 (Oct. 1997).
Reichle et al., "Electro-rotation in octopole micro cages," *J. Phys. D: Appl. Phys.*, 32, 2128-2135 (1999).
Reichle et al., "A new microsystem for automated electrorotation measurements using laser tweezers," *Biochimica et Biophysica Acta* 1459, 218-229 (2000).
Schnelle et al., "Dielectric single particle spectroscopy for measurement of dispersion," *Medical and Biological Engineering & Computing*, vol. 37, 264-271 (1999).
Schnelle et al., "Combined dielectrophoretic field cages and laser tweezers for electrrotation," *Applied Physics B, Lasers and Optics*, 70, 267-274 (2000).
Schnelle et al., "Dielectrophoretic manipulation of suspended submicron particles," *Electrophoresis*, 21, p. 66-73 (2000).

(Continued)

*Primary Examiner*—Jon P Weber
*Assistant Examiner*—Paul C. Martin
(74) *Attorney, Agent, or Firm*—Caesar, Rivise, Bernstein, Cohen & Pokotilow, Ltd.

(57) ABSTRACT

A method is described for non-destructive measurement of vitality of biological cells, especially for determination of apoptosis, in which the at least one cell is exposed to high-frequency alternating, especially rotating, electric fields and/or impedance test fields, and at least one rotation measurement, one dielectrophoresis measurement and/or one impedance measurement is performed with the cell for at least one frequency range or individual frequencies, from which at least one measurement parameter is determined that is characteristic of the vitality state of the cell.

9 Claims, 4 Drawing Sheets

OTHER PUBLICATIONS

Smith et al., "Ionomycin releases calcium from the sarcoplasmic reticulum and activates $Na^+/Ca^{2+}$ exchange in vascular smooth muscle cells," *Cell Calcium*, 10, p. 125-134 (1989).

Thompson, "Apoptosis in the Pathogenesis and Treatment of Disease," *Science*, 267, p. 1456-1462 (Mar. 10, 1995).

Verhaegen, "Microscopical Study of Cell Death Via Apoptosis," *European Microscopy and Analysis*, 31-33 (Jan. 1998).

Wang et al., "Changes in membrane dielectric properties of HL-60 cells during genistein-induced apoptosis—significance in discrimination of apoptotic, necrotic and normal cells," *Blood*, vol. 1425, No. 2, p. 311-318 (Oct. 1998) (Abstract).

* cited by examiner

METHOD FOR MEASURING THE VITALITY OF CELLS

BACKGROUND OF THE INVENTION

The invention relates to a method for the non-destructive measurement of the vitality of biological cells, especially for non-destructive determination of apoptosis of cells. The method according to the invention furthermore allows the distinction of apoptotic cells from vital cells and necrotically damaged cells. Furthermore, the present invention relates to a method for identification of substances which influence apoptosis.

In nature, cell death occurs in two different manifestations, as necrosis and apoptosis. Necrosis is cell death caused by an unspecific physical or chemical damage. By injury of the barrier function of the plasma membrane, its semipermeability for ions (especially $Ca^{2+}$, $Na^+$, $K^+$) is disturbed. This results in massive ion and solution influx into the cell, which causes the cell to swell and finally rupture. Thus, compartmentation of the cell is abolished and the cell content is spilled. Subsequently, this process causes inflammatory reactions in the organism. Usually, necrotic damages take place within seconds to minutes.

In contrast to this, apoptosis is a programmed cell death. Apoptosis is an organized process, which is needed during the development and maintenance of an organism to eliminate unwanted or damaged cells without harming the organism in total. It is controlled by receptors (glucocorticoid receptor, TNFR, Fas, NGFR) and usually depends on de novo protein synthesis. Cellular proteases (ICE, caspases) and endonucleases become activated. Since almost all cells of an organism can undergo apoptosis, the trigger of the apoptotic process must be under permanent and strict physiological control. From the pure phenomenological viewpoint, apoptosis can be divided into six successive stages: 1. shrinkage, 2. zeiosis (plasma membrane protuberances), 3. chromatin collapse, 4. collapse of the cellular nucleus, 5. fragmentation of the nucleus into smaller units and fragmentation of cellular DNA, 6. separation of apoptotic vesicles (Thompson, C. B., 1995, Apoptosis in the pathogenesis and treatment of disease, Science 267: 1456-1462). Throughout the entire process, the barrier function of the plasma membrane is maintained. The triggering of apoptosis occurs through both internal signals of the organism as well as through external influences, such as radiation, chemical substances or reagents. Apoptosis is a process the first signs of which may develop only hours later. In contrast to necrotic cells, apoptotic cells are recognized and removed by neighbouring cells or macrophages (Orrenius, S., 1995, Apoptosis: molecular mechanisms and implications for human disease, J. Internal Medicine 237: 529-536). Here, no inflammatory reaction occurs.

Newer studies demonstrate that a multitude of diseases is based on disturbances in the regulation of apoptosis. Diseases associated with blockage of apoptosis include forms of cancer, such as carcinomas with p53 mutations and hormone-dependent tumours; autoimmune diseases, such as rheumatoid arthritis, diabetes mellitus; and viral infections, such as infections with herpes viruses, pox viruses and adenoviruses. Diseases which may be caused by an increased rate of apoptosis include particularly AIDS; neurodegenerative disorders, such as Alzheimer's disease, Parkinson's disease; the effects of toxins, such as liver diseases from large amounts of alcohol (Thompson, C. B., 1995, Apoptosis in the pathogenesis and treatment of disease, Science 267: 1456-1462).

For this reason, a multitude of methods based on apoptosis-specific parameters have been developed for determination of apoptosis. These methods, for example, are based on the determination of the phosphatidylserine portion of the extracellular cell surface by annexin V binding, determination of hypoploid nuclei, determination of cytosolic cytochrome C or caspase concentration, or the determination of caspase activation.

Detection is performed by microscopic, fluorescence-based and biochemical procedures. Electron microscopy and phase contrast microscopy, for example, detect the morphological appearance during apoptosis, such as shrinkage, membrane protuberances, and the presence of micronuclei (S. Verhaegen 1998, Microscopical Study of Cell Death via Apoptosis, European Microscopy and Analysis). However, quantification of apoptosis in a sample by microscopy requires a high degree of judgement on the part of the investigator, and manual counting of the cells after optical evaluation, or suitable image processing software.

A further well-known method for detection of apoptosis in a sample of suspended cells requires the use of a flow cytometer. Here, fluorescence dyes staining DNA are used (K. H. Elstein and R. M. Zucker 1994, Comparison of Cellular and Nuclear Flow Cytometric Techniques for Discriminating Apoptotic Subpopulations, Experimental Cell Research 211, 322-331), or a biochemical method is employed in which the process of DNA fragmentation is visualized by incorporation of nucleotides with fluorescent labels (e.g. TUNNEL method, R. S. Douglas, A. D. Tarshis, C. H. Pletcher, P. C. Nowell and J. S. Moore, 1995, A simplified method for the coordinate examination of apoptosis and surface phenotype of murine lymphocytes, Journal of Immunological Methods 188, 219-228). Also, specific fluorescently labelled probes are used for cell surface molecules. An example of such a probe is fluorescenctly labelled annexin V (G. Koopman, C. P. M. Reutlingsperger, G. A. M. Kuijten, R. M. J. Keeshen, S. T. Pals and M. H. J. van Oers, 1994, Annexin V for Flow Cytometric Detection of Phosphatidylserine Expression on B Cells Undergoing Apoptosis, Blood 84,5, 1415-1420) which binds to phosphatidylserine on the cell surface and thus visualizes the restructuring of the plasma membrane in the early apoptotic stage. However, all flow-cytometric methods for the measurement of apoptosis require calibration of the method and the system. In addition, a high number of cells (approx. $10^6$) is required for analysis.

Other methods for the detection of apoptosis require the destruction of all cells in a sample and the gel-electrophoretic or biochemical detection of DNA fragmentation (M. Leist, F. Gantner, I. Bohlinger, P. G. Germann, G. Tiegs and A. Wendel, 1994, Murine Hepatocyte Apoptosis Induced In Vitro and In Vivo by TNF-a Requires Transcriptional Arrest, The Journal of Immunology 153, 1778-1788). These biochemical methods are procedures with several steps in which several reagents are used. This results in a very long time of analysis of up to 6 hours. In addition, several hundred cells are needed for one analysis.

Due to the relevance of disturbed regulation of apoptosis in association with a multitude of diseases, the study of apoptosis is also a central part of the search for new pharmaceutical agents, of the evaluation of their activity against diseases as well as in environmental analytics. Generally, a compound which influences apoptosis must not only be capable of modulating apoptosis but also of permeating the intact cell membrane. Furthermore it is assumed that a multitude of cellular receptors, proteins, cell components and cofactors influences the process of apoptosis in living cells.

Therefore, a multitude of screening methods has already been developed for the identification of substances which influence apoptosis, which are based on the determination of apoptosis-specific parameters in the cell or in cell-free systems.

For example, WO 98/02579 describes a screening assay for the identification of apoptosis-regulating substances in a cell-free system. Here, several apoptosis-specific parameters, such as cytochrome c or CPP32 protease activity, are determined as measures of apoptosis. For screening, a supernatant obtained at 100,000×g from the cytosol of non-apoptotic cells is employed. The determination of substances influencing apoptosis was performed by addition of test compounds to this supernatant which may have negative, positive or no effect on apoptosis. The results obtained in this way are compared to those of a reference substance.

WO 98/55615 describes a screening assay for determination of therapeutically active substances influencing apoptosis. Cell-free assays are described which are designed to study compounds that compete with cytochrome c for binding to apaf-1. Furthermore, assays for determination of substances influencing apoptosis are also described which are based on the study of the proteolytic cleavage of caspase-3 precursors in presence or absence of potential substances influencing apoptosis.

In WO 99/18856, a method is described for the detection of substances for induction or inhibition of enzymes of the apoptosis cascade, especially caspases. The method is performed with whole cells or tissues. In order to do so, a portion of the cells is treated with the test compounds and fluorescenctly labelled reporter molecules, whereas another fraction is treated only with the reporters, as control. A change in fluorescence compared to the control sample indicates that a substance to be tested influences enzymes of the cascade.

Taken together, all currently known methods for determination of apoptosis or apoptosis-modulating substances have a multitude of disadvantages. Thus, they frequently require a great deal of time due to elaborate experimental steps and in addition require large quantities of, for example, antibodies, dyes and other reagents that can enter the cell. Furthermore, most of the methods are based on final cell lysis, eventually leading to destruction of the cells. Other investigated parameters, such as e.g. annexin V, are not specific for apoptosis, still other methods require a large number of cells. Furthermore, many methods are only suited to study late stages of apoptosis which frequently do not occur in vivo, since the apoptotic cells have already been taken up by neighbouring cells or macrophages by phagocytosis in this stage.

Frequently used cell-free assays, such as the determination of cytochrome c and other apoptosis-specific markers, are not suitable for determination of the ability of substances affecting apoptosis to pass through the intact cell membrane.

Furthermore it is though that different cell types have different receptors and cofactors for modulation of apoptosis. For this reason it is not possible to find specific or organ-specific apoptosis modulators with cell-free assays.

Due to the fact that in most of the known methods the importance of cellular receptors and other cofactors is neglected, the danger of identification of false-positive or false-negative substances influencing apoptosis is high, since these substances do not show any or do not show the expected effect in living cells. In addition, substances influencing apoptosis that modulate apoptosis indirectly through one of these receptors or cofactors are not detected.

Considering these disadvantages of the known methods, it would be desirable to have a method available that is suitable for the unambiguous identification of apoptosis and determination of substances which modulate apoptosis. This method should be able to recognize apoptosis in an early stage, and should be easily performable, even with whole cells.

Dielectrophoretic techniques, such as e.g. the dielectric single particle spectroscopy (R. Pethig and G. H. Markx, 1997, Applications of dielectrophoresis in biotechnology, Trends in Biotechnology 15, 426-432) and electrorotation (T. Schnelle, T. Müller and G. Fuhr, 1999, Dielectric single particle spectroscopy for measurement of dispersion, Medical & Biological Engineering & Computing 37, 264-271) are already known as such.

Also, devices for the measurement of electrorotation in combination with the use of optical tweezers are already known (T. Schnelle, T. Müller, C. Reichle and G. Fuhr, 2000, Combined dielectrophoretic field cages and laser tweezers for electrorotation, Applied Physics B, Lasers and Optics, Springer-Verlag) and automatic signal uptake (C. Reichle, T. Müller, T. Schnelle and G. Fuhr, 1999, Electro-rotation in octopole micro cages, Journal of Physics D: Applied Physics 32, 2128-2135; De Gasparis, Wang, Yang, Becker and Gascoyne, 1998, Meas. Sci. Technol. 9, 518-529).

The object of the present invention is to provide an improved method for non-destructive measurement of vitality, especially for the detection of apoptosis, in biological cells. The invention is intended to allow the provision of an improved method for identification of substances influencing apoptosis.

SUMMARY OF THE INVENTION

The basic idea of the invention is the provision of a method for non-destructive measurement of vitality of cells by introducing at least one cell to be examined in a microsystem, in which the at least one cell is exposed to high frequency electric rotating fields or electric alternating fields, especially impedance test fields.

This method particularly allows for differentiation between vital cells, necrotic cells and cells that are in the state of apoptosis.

The invention includes in its preferred embodiments methods for detection of apoptosis in suspended cells by dielectrophoretic techniques.

DETAILED DESCRIPTION OF THE INVENTION

A distinction especially between vital, necrotic and apoptotic cells is not possible with the usual described methods.

Furthermore, the method according to the invention has many advantages compared to the methods that are already known. For example, the necessity of specific detection reagents as well as the resulting time consumed in preparing the samples by processes that frequently include several steps, and elaborate image analysis are eliminated. In addition, the method according to the invention is characterized by single cell-sensitivity, specificity for the apoptotic process, and allows for distinction between necrotic and apoptotic cells, the detection and the automatic and fast determination of apoptosis at an early stage. For the determination, the cells solely are to be present in a suspended state. The addition of one or more reagents is not required. The effort in sample preparation is therefore very small. The method is not limited with respect to the number of cells; the procedure can be performed with individual cells. The individual measurement is very fast (e.g. 30 seconds for electrorotation) and recording a time course in a single cell sample or a single cell is possible. In addition, the method has no measurable influence on the vitality of the cells.

The method according to the invention for non-destructive determination of apoptosis at an early stage is characterized by the at least one cell being introduced to a microsystem in which the at least one cell is exposed to high frequency alternating fields, especially rotating electric fields and/or impedance test fields.

It is preferred that at least one rotational measurement, dielectrophoretic measurement and/or impedance measurement is performed with the cell for at least one frequency range or individual frequencies, resulting in determination of at least one measurement parameter which is characteristic for the vitality state of the cell.

In another embodiment of the method according to the invention, at least one rotational measurement, dielectrophoretic measurement and/or impedance measurement is performed with the minimum of a single cell for at least two frequency ranges or at least two frequencies, resulting in at least two values for the measurement parameter, this minimum of two values being compared to each other, thus leading to a determination of the state of vitality of the cell, particularly if it is a cell in the state of apoptosis, necrosis or if it is a vital cell. Hereby it is especially preferred that the measurement parameter comprises rotation speed, migration speed, electrophoretic mobility and/or impedance, especially amplitude and/or phase.

The embodiment described here has the particular advantage that only a minimum of two values have to be determined for one measurement parameter, and therefore a significant amount of time is saved compared to the recording of an entire spectrum. Therefore, this embodiment is especially suited for high throughput screening.

Especially preferred is the determination of a rotation spectrum of the cell by measuring the rotation speed (inverse rotation time) of the at least one cell based on the frequency of the rotating electric field, whereby it is desirable that the at least one cell is concomitantly held in the focus of an optical trap, especially optical tweezers, during recording of the rotation speed. The rotation measurement is performed preferably with cells suspended in physiological solutions. The conductivity of the solution is preferably in the range of 1 . . . 1.6 S/m.

However it is not necessary to record complete spectra. In fact it is sufficient to perform the measurements with one or more fixed frequencies of the rotating field, preferably with one frequency each of the frequency range of 1 to 4 MHz, preferably 2 to 3 MHz, especially preferred 2.3 to 2.6 MHz and the frequency range 5 to 100 MHz, preferably 6 to 50 MHz, especially preferred 8 to 15 MHz.

To determine if an examined cell is in the state of apoptosis, the rotation speed determined in the higher frequency range is put in relation to the rotation speed determined in the lower frequency range. If the ratio obtained is above 1, especially preferred 1.1 to 1.8, the cell to be analyzed is an apoptotic cell. For necrotic cells, the ratio is below 1, especially preferred 0.6 to 0.8, and for vital cells it is equal to 1.

For determination of apoptosis it is also possible to compare the rotation spectrum of the at least one cell to be analyzed with the rotation spectrum of a reference cell, the reference cell possibly being a vital cell, preferably of the same cell type as the cell to be analyzed. However, it is also desirable that the reference cell is a cell which has specifically been transferred to the state of apoptosis and which is preferably of the same cell type as the cell to be analyzed, or that the reference cell is a cell which has specifically been transferred to the state of necrosis and which is preferably of the same cell type as the cell to be analyzed.

The state of apoptosis can then be preferably determined by the rotation spectrum of the cell to be analyzed in contrast to the vital or necrotic reference cell or comparable with the apoptotic reference cell having its maximum in the frequency range of 5 to 100 MHz, preferably 6 to 50 MHz, especially preferred 8 to 15 MHz.

Another embodiment of the method according to the invention is based on the different behaviour of normal, necrotic and apoptotic cells in dielectrophoresis (DEP).

For determination of apoptosis according to the invention, it may therefore be also desirable to detect a dielectrophoresis spectrum, preferably in the frequency range of 0 to 5 MHz, especially preferred of 1 to 4 MHz, by measuring the migration speed or the electrophoretic mobility of the at least one cell in dependence on the frequency of the electric field, whereby in a special embodiment the at least one cell being held in focus of an optical trap. According to the invention, apoptosis is detected by the frequency change of the transition from negative to positive dielectrophoresis in the dielectrophoresis spectrum being in the range of 3.3 to 3.8 MHz, preferably at 3.5 MHz.

However it may also be desirable to determine the migration speed or the electrophoretic mobility of the at least one cell only with at least 2 frequencies of the frequency range of 0-5 MHz, preferably 1-4 MHz.

If the frequency crossing of the transition from negative to positive dielectrophoresis is 2.8 to 3.1 MHz, preferably 3 MHz, the cell to be analyzed is a vital cell; if it is 1.8 to 2.2 MHz, preferably 2 MHz, the cell to be analyzed is a necrotic cell.

In addition, apoptosis may be determined by the dielectrophoresis spectrum and/or the at least 2 migration speeds or electrophoretic mobilities of the at least one cell to be analyzed being compared to the dielectrophoresis spectrum and/or the at least 2 migration speeds or electrophoretic mobilities of a reference cell, the reference cell possibly being a vital cell, preferably of the same cell type as the cell to be analyzed. However, it is also desirable that the reference cell is a cell which has been specifically transferred to the state of apoptosis, preferably a cell of the same cell type as the cell to be analyzed, or that the reference cell is a cell which has been specifically transferred to the state of necrosis, preferably a cell of the same cell type as the cell to be analyzed.

In a further embodiment of the present invention, the different forces which act upon vital, apoptotic and necrotic cells in an alternating electric field are used to separate the different cell types. The increase in the internal conductivity and the dielectric constant of necrotic cells compared to vital cells results in modified values of the real part of the electric dipole moment. The force acting on necrotic cells compared to vital and apoptotic cells is markedly decreased in PBS buffer preferably in the frequency range over 1 MHz (FIG. 5), and thus, dielectric separation is possible.

A decrease in the electrolyte content of the buffer solution below a range around 0.3 S/m results preferably in a frequency range up to 3 MHz for apoptotic and necrotic cells in a lower negative DEP compared to vital cells. In contrast to this, a strongly decreased positive DEP of apoptotic and normal cells compared to necrotic cells develops in a frequency range of 3 to 120 MHz. The frequency crossing at the transition from negative to positive DEP is here in the range from 3.3 to 3.8 MHz for apoptotic cells, preferably 3.5 MHz, for vital cells in the range of 2.8 to 3.1 MHz, preferably 3 MHz, and for necrotic cells in the range of 1.8 to 2.2 MHz, preferably 2 MHz. Thus, an effective separation of all three cell types is possible by dielectrophoretic forces. In this way, the proportions of necrotic, apoptotic and vital cells of a sample can be determined (FIG. 5B).

According to another embodiment of the method according to the invention, the determination of apoptosis may also be performed by measurement of the impedance property, especially amplitude and/or phase, of the at least one cell based on the frequency of the impedance test field. An impedance spectrum is determined, the at least one cell preferably being held in focus by an optical trap. It is also desirable that the impedance of individual cells is determined between microelectrodes in small volumes. Furthermore it is preferred that the impedance of the at least one cell is recorded at at least two frequencies in the frequency range of 1 Hz to 100 kHz, preferably 0.5 kHz to 10 kHz. The impedance of a cell suspension is calculated as follows:

$$Z(\omega) = \frac{1}{\left(\frac{1}{R_{ext}} + \frac{1}{R_c + \frac{1}{1\omega C_M}}\right)}$$

(Fricke, H., 1923, The electric capacity of cell suspensions, Phys. Rev. 21, 708-709), with $R_{ext}$ being the external solution resistance, $R_c$ being the cytoplasm resistance and $C_M$ being the membrane capacity. For an accurate analysis of biological cells, complex models are required which reflect the capacity and Ohmic portions of all compartments (Irimajiri, A., Suzaki, T., Asami, K. and Hanai, T., 1991, Dielectric Modeling of Biological Cells. Models and Algorithm, Bull. Inst. Chem. Res. Kyoto Univ. 69/4, p. 421-438).

In order to guarantee high sensitivity of the measurement according to the invention, it is desirable that the contribution of the solution $1/R_{ext}$ is small compared to the contribution of the individual cell. This applies either to small frequencies or for a small distance between the cell and the measuring electrodes which are also small (single cell impedance measurement), the single impedance measurement for determination of differences in cytoplasmic properties in the megahertz range being especially desirable. In addition, the cellular modifications during apoptosis result in a modified impedance signal in the lower frequency range: 1 Hz-100 kHz, preferably 0.5 kHz-10 kHz. For determination of apoptosis it is therefore preferred to record impedance spectra in this frequency range.

For determination of apoptosis it is also possible that the impedance spectrum and/or the at least 2 impedances (value and/or phase) of the at least one cell to be analyzed is compared with the impedance spectrum and/or the at least 2 impedances (value and/or phase) of a reference cell, the reference cell possibly being a vital cell of preferably the same cell type as the cell to be analyzed. However, it is also desirable that the reference cell is a cell which has been specifically transferred to the state of apoptosis, preferably a cell of the same cell type as the cell to be analyzed, or that the reference cell is a cell which has been specifically transferred to the state of necrosis, preferably a cell of the same cell type as the cell to be analyzed.

The state of apoptosis can be then preferably be determined by the impedance spectrum and/or the at least 2 impedances of the cell to be analyzed in contrast to the vital or necrotic reference cell, or comparable to the apoptotic reference cell show changes especially in the frequency range of 1 Hz-100 kHz, preferably 0.5 kHz-10 kHz.

To follow the change over time of the properties of the at least one cell, especially for determination of the time course of apoptosis, it may be desirable that the rotation spectrum and/or the at least 2 rotation speeds and/or the dielectrophoresis spectra and/or the at least 2 migration speeds or electrophoretic mobilities and/or the impedance spectra and/or the at least 2 impedances are recorded in dependence on time.

In a preferred embodiment of the method according to the invention, the following procedure is provided:
Providing at least one cell sample to be analyzed,
Introduction of the at least one cell of the cell sample to be analyzed in a microsystem and detection of the at least one measurement parameter which is characteristic for the vitality condition of the cell,
Separation of the cells of the cell sample to be analyzed or a certain volume of this cell sample according to their vitality state.

In summary, the method according to the invention is especially suited for diagnosis and/or therapeutic control of diseases and/or processes which are associated with an increase in the apoptosis rate, such as particularly AIDS, neurodegenerative diseases, particularly Alzheimer's disease, Parkinson's disease; liver diseases caused by toxins, particularly alcohol, diseases resulting from a hormone production or secretion deficiency.

According to the invention it is also possible to use the method for detection of apoptosis for diagnosis and/or therapeutic control of diseases and/or processes which are associated with a decrease in the apoptosis rate, such as particularly malignant and benign hyperproliferative diseases such as cancer, hormone-dependent tumours, leukaemia, autoimmune diseases, particularly arthritis, diabetes mellitus and viral infections, particularly those caused by herpes viruses, pox viruses or adenoviruses.

The method according to the invention furthermore allows a rapid performance, and low number of cells is needed for analysis. The method can even be performed with a single cell. It is therefore very well suited for therapy control particularly of malign and benign hyperproliferative diseases during chemotherapy, radiation therapy, immunotherapy, surgery or a combination of these therapies.

According to the invention it was also possible to provide a method that allows for the identification of substances which influence apoptosis, taking into account the cellular receptors and other cofactors, and which therefore reduces the risk of identification of false-positive or false-negative substances influencing apoptosis.

A method according to the invention for identification of apoptosis-influencing substances is characterized particularly by the following steps:
Providing of at least one cell culture sample to be analyzed,
Addition of a potential substance influencing apoptosis or mixtures of at least two of these substances,
Introduction of at least one cell of the cell culture sample to be analyzed in a microsystem and determination of at least one measurement parameter which is characteristic for the vitality state of the cell, the at least one cell being exposed to high frequency, alternating, particularly rotating, electrical fields and/or impedance test fields.
Determination of the effects on apoptosis, especially by comparing the behaviour of this at least one cell in the electrical field with the behaviour of the at least one cell of a reference sample.

In a preferred embodiment, at least two values are determined for one measurement parameter, and the effects on apoptosis are determined by comparing these at at least two values. Furthermore, the effects on apoptosis are determined by comparing at least one value for one measurement parameter of the at least one cell with the at least one value of the at least one cell of a reference sample.

It is preferred to use, as the reference sample, a sample of the same cell type as the sample to be analyzed before addition of the at least one potential substance influencing apoptosis.

In another embodiment of the method according to the invention, the behaviour of the at least one cell of the cell culture sample to be analyzed and the at least one cell of the reference sample are examined in the electrical field by recording a rotation spectrum by measurement of the rotation speed of each cell in dependence on the frequency of the rotating electrical fields.

The effects on apoptosis of at least one substance can be detected according to the invention by the rotation spectrum of the at least one cell to be analyzed of the sample in contrast to the spectrum of the at least one cell of the reference sample demonstrating a change especially in the frequency range of 5 to 100, preferably 6 to 50 MHz, especially preferred 8 to 15 MHz and/or in the frequency range of 1 to 4 MHz, preferably 2 to 3 MHz, especially preferably 2.3 to 2.6 MHz.

It may, however, also be preferred that the rotation speed of the cells of the cell sample and the reference is determined only at at least one frequency each of the frequency range of 1 to 4 MHz, preferably 2 to 3 MHz, especially preferred 2.3 to 2.5 MHz, and the frequency range 5 to 100 MHz, preferably 6 to 50 MHz, especially preferred 8 to 15 MHz, the rotation speed determined at the higher frequency range being put in relation to the rotation speed which is determined in the lower frequency range.

For an apoptotic cell, the ratio is greater than 1, especially preferred 1.1 to 1.8; for a necrotic cell smaller than 1, especially preferred 0.6 to 0.8 and for a vital cell equal to 1.

However, it may also be desirable to examine the behaviour of the at least one cell of the cell culture sample to be analyzed and the at least one cell of the reference sample in the electric fields by recording a dielectrophoresis spectrum by measurement of the migration speed or the dielectric mobility of each cell based in the frequency of the alternating electrical fields.

a further embodiment of the method, the effects on apoptosis of the at least one substance are determined by the frequency change from negative to positive dielectrophoresis in the dielectrophoresis spectrum of the at least one cell to be analyzed on contrast to the spectrum of the at least one cell of the reference sample being in the range of 3.3 to 3.8 MHz, preferably 3.5 MHz, the dielectrophoresis spectrum of the at least one cell to be analyzed being recorded in the frequency range of 0 to 5 MHz, preferably 1 to 4 MHz.

In a further embodiment of the method according to the invention, the behaviour of the at least one cell of the cell culture sample to be analyzed and the at least one cell of the reference sample in the electric field is examined by recording an impedance spectrum by measurement of the impedance properties (value and/or phase) of each cell based on the frequency of the impedance test field.

A further embodiment of the method describes that the effects on apoptosis of the at least one substance can be determined by changes occurring in the frequency range of 1 Hz to 100 kHz, preferably 0.5 kHz to 10 kHz in the impedance spectrum of the at least one cell to be analyzed in contrast to the spectrum of the at least one cell of the reference sample.

During recording of the rotation spectrum at at least one frequency and/or a dielectrophoresis spectrum and/or an impedance spectrum, it may be desirable that the at least one cell is held in the focus of an optical trap.

For determination of the influence of potential substances influencing apoptosis it may be preferred to determine the proportion of apoptotic cells in a sample. For this purpose, a separation of the cells of a certain sample volume and/or of a certain volume of the reference sample may be conducted first. The separation can be conducted dielectrophoretically. Then, the number of apoptotic cells of the sample to be analyzed is determined in relation to the number of apoptotic cells in the reference sample.

Thus, substances which increase apoptosis are characterized by an increase in the number of apoptotic cells in relation to the reference sample.

Substances that do not influence apoptosis are characterized by a number of apoptotic cells that is comparable to the reference sample.

Thus, substances which inhibit apoptosis are characterized by a smaller number of apoptotic cells in relation to the reference sample.

Since the natural apoptosis rate in cell cultures often is very small, it may also be desirable in determining potential apoptosis-inhibiting substances to add an apoptosis-increasing substance to the cell culture sample to be analyzed, either before or during the addition of the at least one substance to be analyzed, the cell culture sample which had been supplemented with an apoptosis-increasing substance and/or a cell cultures sample containing the same amount of apoptosis-increasing substance being used as reference sample.

A substance which decreases apoptosis is characterized by containing a smaller number of apoptotic cells in relation to the reference sample.

In summary, the determination of apoptosis according to the present invention allows for the determination of apoptosis with a simple, efficient, fast and high throughput method by recognizing early stages of apoptosis without destroying the cell. A further advantage of the method according to the invention is that this method can be applied to cells in their physiological environment without changing the properties of the cells or its surface. The methods for determination of substances influencing apoptosis are capable of exactly measuring their ability to enter the cell, taking into account the influence of receptors and cofactors. The risk of a false-positive or false-negative determination of substances influencing apoptosis is significantly lower compared to the known methods. In addition, it is possible to determine cell type- or organ-specific modulators. Furthermore, no specific cell membrane-permeating fluorescent dyes are required for the application of the method according to the invention.

BRIEF DESCRIPTION OF THE DRAWINGS

In FIG. 5, electrorotation and dielectrophoresis of T lymphocytes (Jurkat) based in the field frequency are shown. Curves a, b and c belong to normal, necrotic and apoptotic cells, respectively. In A, automatic measurements of the electrorotation in PBS (conductivity 1.5 S/m) as well as curve fits according to multishell spherical models with dispersion are shown. B shows the corresponding dielectrophoretic behaviour, with the curves' indices corresponding to different external conductivities (1: 0.05 S/m, 2: 0.3 S/m, 3: 1.5 S/m (PBS)).

The dispersive material behaviour is described as the sum of relaxations (dielectric constant $\epsilon$, conductivity $\sigma$, angular frequency of the electrical field $\omega$, relaxation time of the dispersion $\tau$, number of dispersions $\eta$):

$$\varepsilon = \varepsilon_\infty + \frac{1}{\varepsilon_{vac}} \sum_{k=1}^{n} \frac{\tau_k \Delta\sigma_2}{1+(\omega\tau_k)^2} \quad \text{with} \quad \Delta\varepsilon = -\Delta\sigma$$

EXAMPLE 1

Electrorotation Measurement

Materials Used

Jurkat cells: Clone E6.1 from the European Collection of Animal Cell Cultures, Salisbury, England;
U937 cells: Monocytic cell line from the European Collection of Animal Cell Cultures, Salisbury, England;
RMA cells: Thymoma cell line from the clone C57/BL6 from Professor Peter Walden, Charité, Berlin, Ref: C. Reichle, K. Sparbier, T. Müller, T. Schnelle, P. Walden and G. Fuhr, in press, Combined laser tweezers and dielectric field cage for the analysis of multivalent receptor ligand interactions on single cells, ELECTROPHORESIS, Miniaturization II;
Actinomycin D: SIGMA Aldrich GmbH, Steinheim, Germany;
Ionomycin: Calbiochem, Bad Soden, Germany;
Propidium iodine: SIGMA Aldrich GmbH, Steinheim, Germany;
PBS: Phosphate buffered saline, with calcium and magnesium, Seromed/Biochrom, Berlin, Germany;
RPMI 1640 medium: HEPES buffered, GIBCO Life Technologies, Karlsruhe, Germany;
Fetal calf serum: Seromed/Biochrom, Berlin, Germany;
Penicillin: Seromed/Biochrom, Berlin, Germany;
Inositol: SIGMA Aldrich GmbH, Steinheim, Germany.

Figure 6:
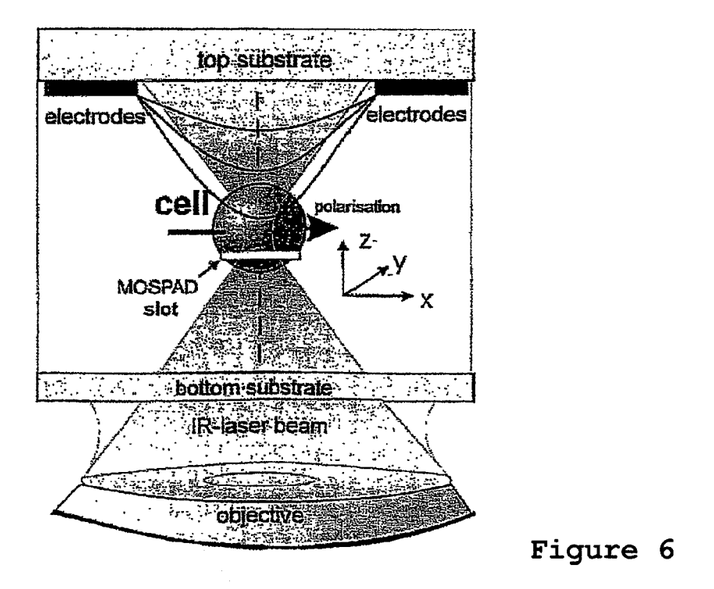
FIG. 6 shows a lateral view of a microsystem for electrorotation measurements in microchannels (C. C. Reichle, T. Schnelle, T. Müller, T. Leya and G. Fuhr, 2000, A new microsystem for automatic electrorotation measurements using laser tweezers, Biochimica et Biophysica Acta 1459, p. 218-229).

Instrument:

An instrument already described by C. C. Reichle, T. Schnelle, T. Müller, T. Leya and G. Fuhr (2000, A new microsystem for automatic electrorotation measurements using laser tweezers, Biochimica et Biophysica Acta 1459, p. 218-229), a combination of dielectrophoretical field cages with optical traps, especially laser tweezers, was used for determination of the electrorotation spectra (FIG. 6). A comparable device is also described in T. Schnelle, T. Müller, C. Reichle and G. Fuhr 2000, Combined dielectrophoretic field cages and laser tweezers for electrorotation, Applied Physics B, Lasers and Optics, Springer Verlag.

Figure 4:
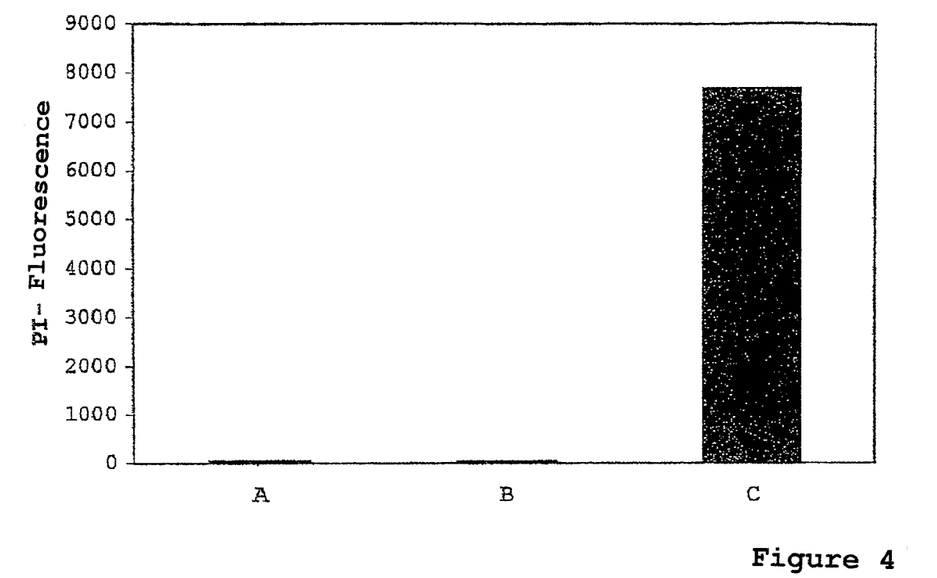
FIG. 4 shows the propidium iodine fluorescence of a normal U937 cell (A), an apoptotic U937 cell (monocytic cell line from the European Collection of Animal Cell Cultures, Salisbury, England) treated with actinomycin D for 4 hours (B), and a necrotic U937 cell (C).
Figure 5:
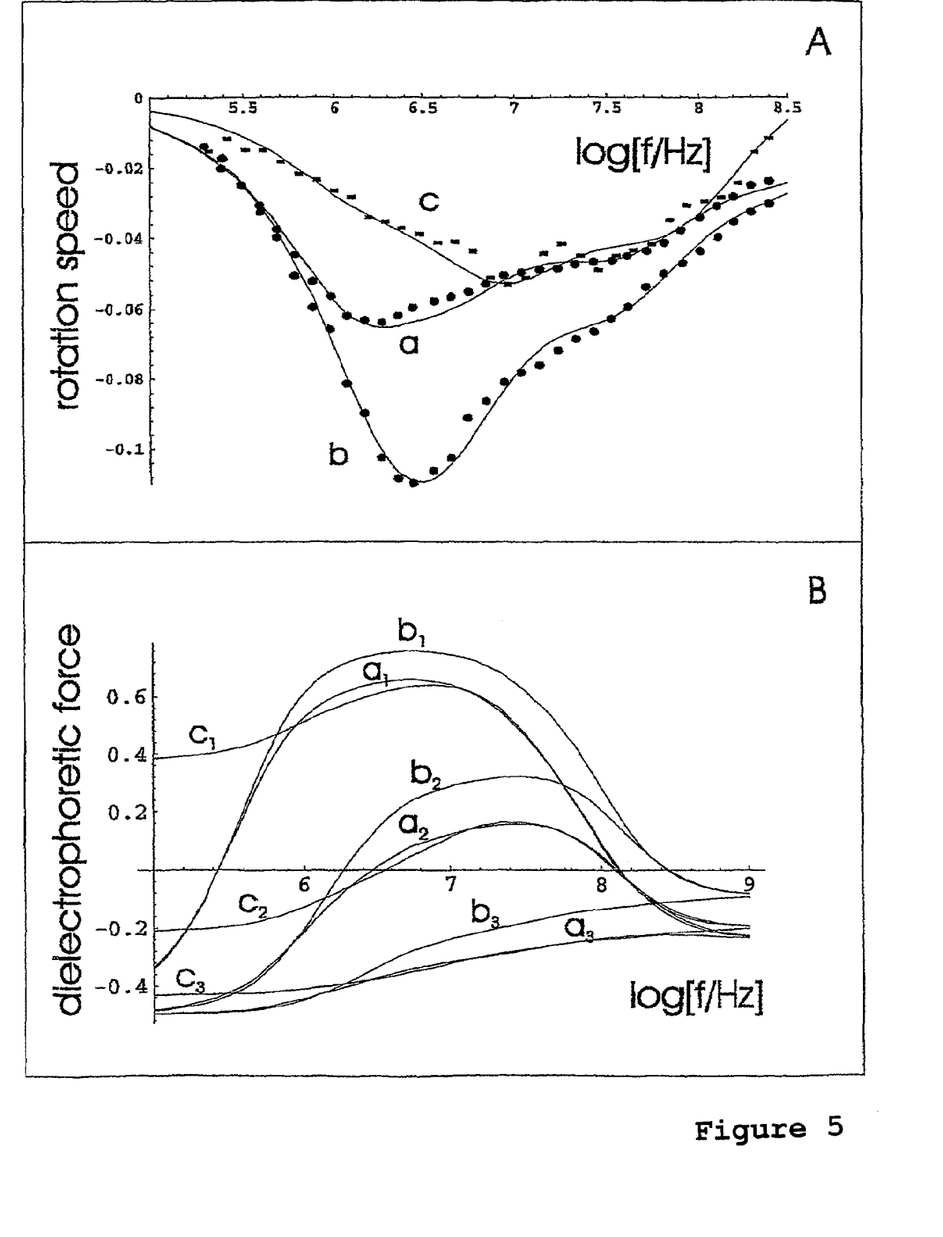

Procedure:

Jurkat T lymphoma cells and U937 monocytic cells were cultivated in RPMI-1640 medium supplemented with 10% fetal calf serum and 100 IU/ml penicillin as well as 100 IU/ml streptomycin. Apoptosis was triggered by addition of 5 µg/ml actinomycin D in a culture that was seeded the day before with $2\times10^5$ cells per ml. The classical morphological changes during apoptosis were documented photographically (see FIG. 1). At different times, an aliquot was taken from the culture, added to a mixture of isotonic phosphate buffer (PBS, D8662 from SIGMA with calcium and magnesium) and, if desired, 0.3 M inositol with correspondingly indicated electrical conductivity, and introduced in a device for measurement of the electrorotation in a microelectrode system. As a control, untreated Jurkat cells were used (FIG. 5). For comparison, electrorotation spectra (ER spectra) were determined from ionomycin-treated cells (10 µg/ml ionomycin) as well as from cells the plasma membrane of which had been damaged by increasing the voltage from 4 V to 6.8 V or a treatment with optical tweezers with 30-60 mW (2.8 A of the 1 W Nd:YAG laser, TEM$_{00}$, 1064 nm, LD 3000i, Laser Quantum Ltd., Manchester, UK, P.A.L.M. System) for 15 minutes. For this, the cells were transferred individually to the center of the quadrupole or octupole of the microelectrode system. For this, optical tweezers with a power of approx. 30 mW were used in the indicated cases at the site of holding. The frequency of the cell rotation was measured either automatically or using a timer (FIG. 2). The uptake of propidium iodine (5 µm) in necrotically damaged cells or comparative measurements with vital and apoptotic cells (FIGS. 3 and 4) was measured by confocal nanofluorometry (Gradl, T. Müller, C. Reichle, T. Schnelle and G. Fuhr, 1999, Micro-Electrode Systems for Cell Analysis, European Journal of Cell Biology, Suppl. 49, Vol. 78; T. Schnelle, T. Müller, G. Gradl, S. G. Shirley and G. Fuhr, 2000, Dielectrophoretic manipulation of suspended submicron particles, ELECTROPHORESIS 2000, 21, p. 66-73).

Electrorotation Measurement:

The device for measurement of the electrorotation was attached to a fluorescence correlation spectrometer. The cells were made visible over a 40×W 1.2 NA lens. They were excited with 1.5 µW by a helium-neon laser with a wavelength of 543 nm and the radiated fluorescence was passed through a 585 DF 35 band pass filter over a 50 µm pinhole to a photodiode, with which the fluorescence photons were counted.

Figure 1:
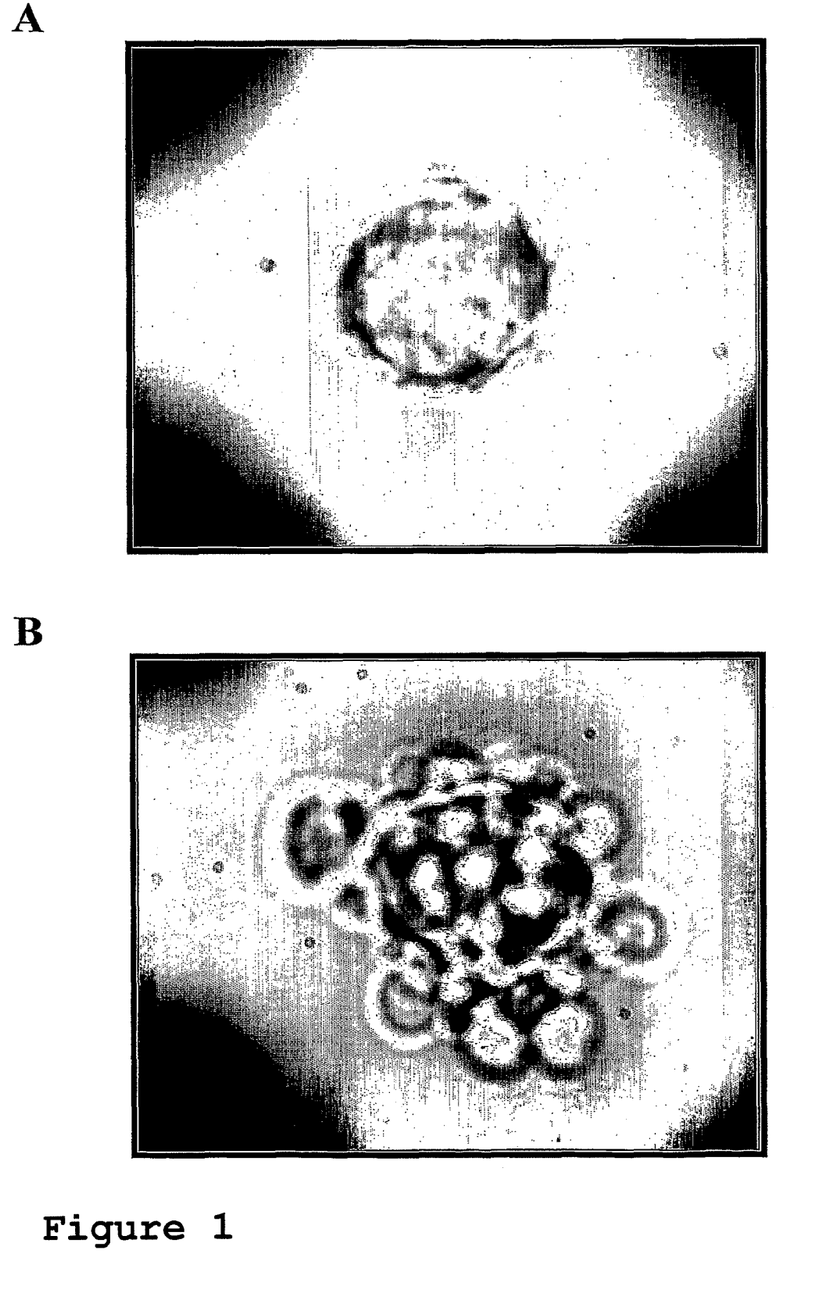
FIG. 1 shows light-microscopic images of a normal (A) and an apoptotic (B) Jurkat cell (clone E6.1 from the European Collection of Animal Cell Cultures, Salisbury, England). The apoptotic cell was treated with 5 µg/ml actinomycin D for 4 hrs.
Figure 2:
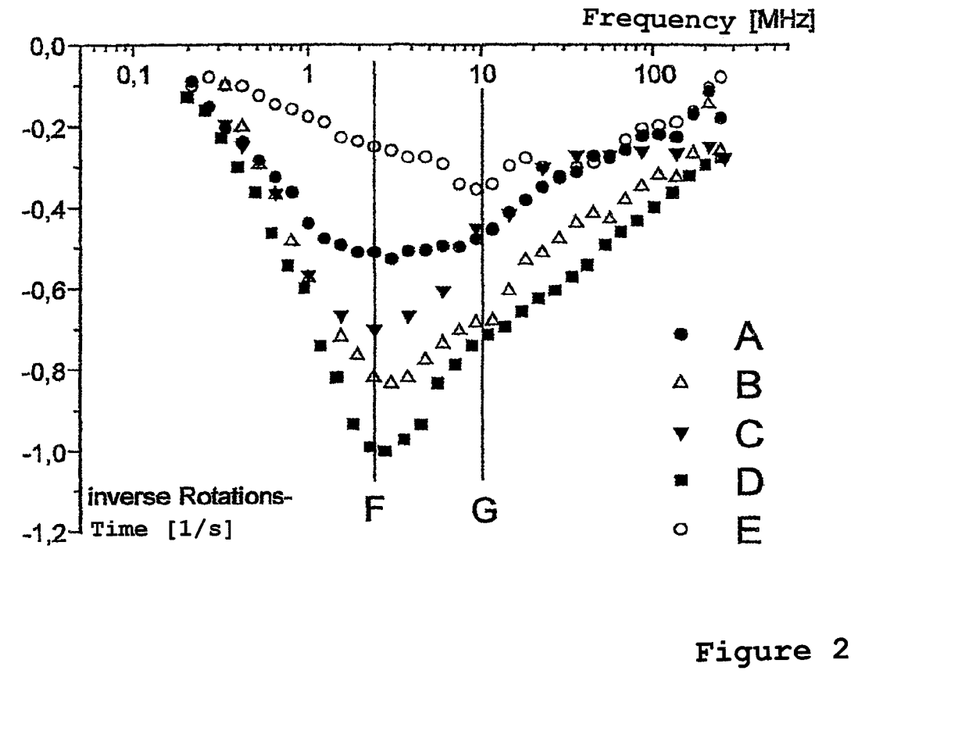
FIG. 2 shows electrorotation spectra of a normal Jurkat cell (A), a Jurkat cell that has been treated with 10 µm ionomycin for approx. 5 min (B), a Jurkat cell that has been damaged dielectrophoretically with 50 kHz and Erms=30 kV/m for 20 seconds (C), an RMA cell that has been held with 30 mW of optical tweezers of 1080 nm wavelength for 40 min (thymoma cell line from the clone C57BL/6 from Professor Peter Walden, Charité, Berlin) (D) and a Jurkat cell that has been treated for 4 hours with actinomycin D (E).

Result:

The characteristic ER spectrum of a normal (A) Jurkat cell shown in FIG. 1 demonstrates a wide peak of 1.5 to 7 MHz, during which a maximal rotation speed of the cell is measured, with a maximum around 2.5 MHz (FIG. 2A). A cell treated with the ionophore ionomycin (Calbiochem, Bad Soden, Germany) gives a markedly different ER spectrum from a normal cell (FIG. 2B). Ionomycin at a higher concentration induces the uptake of calcium from the extracellular space into the cell (J. B. Smith, T. Zheng and R. M. Lyu, 1989, Ionomycin releases calcium from the sarcoplasmic reticulum and activates $Na^+/Ca^{2+}$ exchange in vascular smooth muscle cells, Cell Calcium 10, p. 125-134). At the ionomycin concentration of 10 μM, the fits of the corresponding spectra show that in addition, uptake of water and probably also of buffer ions in substantial amounts, such as sodium and potassium, takes place. This can be seen clearly from the increase in conductivity σ (as sum of $\sigma_0$, $\Delta\sigma_1$ and $\Delta\sigma_2$) from 0.77 to 1.15 s $m^{-1}$ and the dielectric constant $\epsilon_\infty$ from 45 to 75 in the cell (C. Reichle, T. Schnelle, T. Müller, T. LEya and G. Fuhr, 2000, A new microsystem for automated electrorotation measurements using laser tweezers, Biochimica et Biophysica Acta 1459, p. 218-229). They approximate the values of the surrounding buffer PBS.

Figure 3:
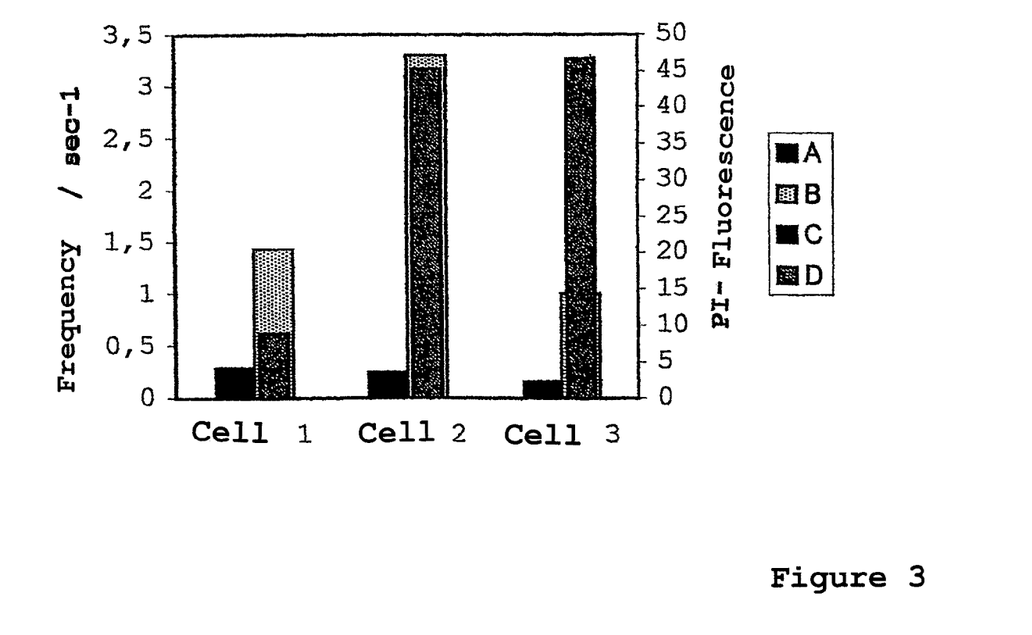
In FIG. 3, the acceleration of the electrorotation and uptake of propidium iodine during necrotic damaging of Jurkat cells by increase of voltage in a dielectrophoretic octupole field cage is shown. (A) rotation speed (inverse rotation time) of a Jurkat cell at 4.3 V, (B) Frequency of rotation of the same Jurkat cell after increasing the voltage to 6.8 V. (C) Propidium iodine fluorescence of the Jurkat cell at 4.3 V, (D) Propidium iodine fluorescence of the same Jurkat cell after increasing the voltage to 6.8 V. Each time, the electrorotation was measured with 4.3 V. Three different cells were analyzed.

Since the dielectrically active total concentration of sodium and potassium ions of a cell before the treatment is lower than the ion concentration of the PBS (phosphate buffered saline, with calcium and magnesium, Seromed/Biochrom, Berlin, Germany), approx. 0.54 S/m vs. 1.5 S/m; a net influx of ions and water occurs and the cell swells. In the ER spectrum, this is reflected in a great enlargement of the 2.5 MHz peak, and can be explained by an approx. 40% increase in the HF conductivity and a more than 60% increase of the dielectric constant of the cytoplasm. Cells that have experienced necrotic damage by application of an increased voltage in the dielectric field cage show very similar behavior (FIG. 2C). This dielectric breakthrough is associated with damage of the plasma membrane, which can be made visible by the uptake of the DNA dye propidium iodine (FIG. 3). Subsequently ions can exchange between the internal cellular space and the surrounding buffer here as well. The resulting ER spectrum is very similar to the spectrum of a cell treated with ionomycin. A necrotic damage with optic tweezers also results in the same phenomenon (FIG. 2D). All described damage up to here is associated with a loss of the integrity of the plasma membrane and an approach of the ion content of the internal to that of the external cellular spaces. If the conductivity of the external solution decreases to a value below the conductivity of the cell, a net efflux of ions would decrease the electrolyte content of the cell. This results in a further decrease in the frequency with the fastest rotation ($f_c$) and enhances the differences compared to the untreated cells. Surprisingly, a characteristic spectrum of an apoptotic cell is different from the spectrum of a normal cell or the spectrum of a necrotically damaged cell (FIG. 2E). The peak at 2.5 MHz disappears completely. The highest rotation speed occurs at approx. 10 MHz. A typical apoptotic cell with this described ER spectrum has strong plasma protuberances (see FIG. 1B). In this stage, however, its plasma membrane is still intact (FIG. 4). Thus, the method according to the invention is suited to distinguish between normal, apoptotic and necrotically damaged cells.

Electrorotation measurements at the two frequencies 2.5 MHz (FIG. 2F) and 10 MHz (FIG. 2G) can already demonstrate clearly the difference between these three different cell states. The ratio between the rotation speed (inverse rotation time) of the measurement at 10 MHz and the measurement at 2.5 MHz is for the normal cell near 1 (with a deviation of approx. 10%). For the necrotically damaged cell it is clearly smaller than 1 (0.6-0.8) and for the apoptotic cell it is higher than 1 (in this case 1.4).

The invention claimed is:

1. A method for non-destructive measurement of three different vitality states of biological cells, comprising the steps of:
   exposing the cells to high-frequency, alternating electric fields or impedance test fields,
   determining a first rotation speed of at least one cell at at least one first frequency within a first frequency range from 1 to 4 MHz,
   determining a second rotation speed of the at least one cell at at least one second frequency within a second frequency range from 5 to 100 MHz, and
   determining a quotient of the second rotation speed divided by the first rotation speed, wherein said quotient is characteristic for at least one of the three different vitality states of the cell, so as to identify at least one cell in a state of apoptosis, at least one cell in a state of necrosis, and at least one cell in a vital state.

2. The method according to claim 1, wherein an apoptotic cell is determined by said quotient being greater than one, a necrotic cell is determined by said quotient being less than 1, and a vital cell is determined by said quotient being equal to 1.

3. The method according to claim 2, wherein the quotient for apoptotic cells is 1.1 to 1.8, and the quotient for necrotic cells is 0.6 to 0.8.

4. The method according to claim 1, wherein said apoptosis is determined by at least two rotation speeds of at least one cell to be analyzed being compared to at least two reference rotation speeds of a reference cell determined at the same frequencies as the cell to be analyzed.

5. The method according to claim 4, wherein the reference cell is of the same cell type as the cell to be analyzed, and is a vital cell, a cell that has been specifically placed in an apoptotic state, or a cell that has been specifically placed in a necrotic state.

6. A method of identifying apoptosis-influencing substances, said method comprising the following steps:
   providing at least one cell culture sample to be analyzed,
   addition to the at least one cell culture sample of at least one substance potentially influencing apoptosis,
   introduction of the at least one cell culture sample to be analyzed into a microsystem for determining rotation speeds of the at least one cell,
   exposing the at least one cell of the cell to high-frequency, alternating electric fields or impedance test fields,
   determining a first rotation speed of at least one cell at at least one first frequency within a first frequency range from 1 to 4 MHz,
   determining a second rotation speed of the at least one cell at at least one second frequency within a second frequency range from 5 to 100 MHz, and
   determining a quotient of the second rotation speed divided by the first rotation speed, wherein said quotient is characteristic for at least one of the three different vitality states of the cell, so as to identify whether the at least one cell is in a state of apoptosis, a state of necrosis, or a vital state, and to thereby identify whether the at least one substance influences apoptosis.

7. The method according to claim 6, wherein prior to addition of the at least one potential apoptosis-influencing substance, a sample of a same cell type as the sample to be analyzed is used as a reference sample.

8. The method according to claim 6, wherein an apoptotic cell is determined by said quotient being greater than 1, a necrotic cell is determined by said quotient being less than 1, and a vital cell is determined by said quotient being equal to 1.

9. The method according to claim 8, wherein the quotient for apoptotic cells is 1.1 to 1.8, and the quotient for necrotic cells is 0.6 to 0.8.

* * * * *